(12) United States Patent
Osterwalder et al.

(10) Patent No.: US 11,753,420 B2
(45) Date of Patent: Sep. 12, 2023

(54) LOW HALIDE LANTHANUM PRECURSORS FOR VAPOR DEPOSITION

(71) Applicant: Versum Materials US, LLC, Tempe, AZ (US)

(72) Inventors: Neil Osterwalder, Carlsbad, CA (US); Sergei V. Ivanov, Schnecksville, PA (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 0 days.

(21) Appl. No.: 17/394,328

(22) Filed: Aug. 4, 2021

(65) Prior Publication Data

US 2021/0363162 A1 Nov. 25, 2021

Related U.S. Application Data

(62) Division of application No. 16/685,266, filed on Nov. 15, 2019, now abandoned.

(60) Provisional application No. 62/772,450, filed on Nov. 28, 2018.

(51) Int. Cl.
*C07F 5/00* (2006.01)
*B01D 7/00* (2006.01)

(52) U.S. Cl.
CPC . *C07F 5/00* (2013.01); *B01D 7/00* (2013.01)

(58) Field of Classification Search
None
See application file for complete search history.

(56) References Cited

U.S. PATENT DOCUMENTS

| 2,743,169 | A | 4/1956 | Hecker |
| 4,478,600 | A | 10/1984 | Schoener et al. |
| 5,951,820 | A | 9/1999 | Ohsaki et al. |
| 2006/0141155 | A1 | 6/2006 | Gordon et al. |
| 2007/0231241 | A1 | 10/2007 | Suzuki |
| 2013/0211117 | A1 | 8/2013 | Modtland |
| 2013/0312855 | A1 | 11/2013 | Birtcher |
| 2016/0175736 | A1 | 6/2016 | Stoessel et al. |
| 2021/0363162 | A1* | 11/2021 | Osterwalder ..... C23C 16/45553 |

FOREIGN PATENT DOCUMENTS

| CN | 102312214 | * | 1/2012 | ............. C23C 16/18 |
| CN | 102924207 | * | 2/2013 | ............. C07B 63/00 |
| CN | 102977132 | * | 3/2013 | ................ C07F 5/00 |
| CN | 103628037 | * | 3/2014 | ............. C23C 16/40 |
| CN | 104218189 | * | 12/2014 | ............. B01D 7/00 |
| CN | 104383712 | * | 3/2015 | ............. B01D 7/00 |
| CN | 104667562 | * | 6/2015 | ............. B01D 7/00 |
| CN | 105315117 | * | 2/2016 | ............. B01D 3/00 |

(Continued)

OTHER PUBLICATIONS

Mullin ("Sublimation" Ullmann's Encyclopedia of Industrial Chemistry, first published Jan. 15, 2003, downloaded from https://doi.org/10.1002/14356007.b03_05 on Oct. 5, 2022) (Year: 2003).*

(Continued)

*Primary Examiner* — Amy C Bonaparte
(74) *Attorney, Agent, or Firm* — Daniel A. DeMarah, Jr.

(57) ABSTRACT

Lanthanide compounds for vapor deposition having ≤50.0 ppm, ≤30.0 ppm, or ≤10.0 ppm of all halide impurity combined is provided. The purification systems and methods are also provided.

13 Claims, 2 Drawing Sheets

(56) References Cited

FOREIGN PATENT DOCUMENTS

| | | | | |
|---|---|---|---|---|
| CN | 106310701 | * | 1/2017 | ............... B01D 7/00 |
| CN | 106474760 | * | 3/2017 | ............... B01D 7/00 |
| CN | 107382778 | * | 11/2017 | ........... C07C 267/00 |
| JP | 2013-49672 A | | 3/2013 | |
| JP | 2013049672 | * | 3/2013 | ................ C07F 5/00 |
| TW | I349043 | * | 9/2011 | ............. C23C 16/16 |

OTHER PUBLICATIONS

Devi, Anjana. "Old Chemistries for New Applications: Perspectives for Development of Precursors for MOCVD and ALD Applications"; Coordination Chemistry Reviews 257 (2013); p. 3332-3384, 2013.

Edelmann, Frank. "Lanthanide Amidinates and Guanidinates: From Laboratory Curiosities to Efficient Homogeneous Catalysts and Precursors for Rare-Earth Oxide Thin Films." Chem Soc. Rev., 2009, 38, p. 2253-2268, 2009.

Johnson "Recent Developments in Molecular Precursors for Atomic Layer Deposition." Organomet Chem., 2019, 42, p. 1-53.

Drose, P. "Structural Investigation of Homoleptic Lanthanide(III)Tris(pivalamidinates), [tBuC(NiPr)2]3Ln (Ln=Ce, Eu, Tb)" Z. Anorg. Allg. Chem. 2011, 637, p. 186-189, p. 188-189 (Year: 2009).

Bochkarev, Mikhail. "Methyl- and propylacetamidinates of lanthanides: Structures, catalytic and some physical properties" Inorganica Chimica Acta, 361, 2008, p. 2533-2539.

Paivasaari, Jani "Synthesis, structure and properties of volatile lanthanide complexes containing amidinate ligands application for Er2O3 thin film growth by atomic layer deposition" Journal of Materials, 2005, 15 p. 4224-4322.

Chervonnyi, A.D. "Thermodynamic Properties of Lanthanum Chlorides" Inorganic Materials, 40, 10, 2004, p. 1097-1104.

B. Lee, et al. "Electrical Properties of atomic-layer-deposited La2 O3 Films Using a novel La formamidinate Precursor and Ozone" Microelectric Engineering, vol. 86, 2009, pp. 1658-1661.

Lim, D. "Electrical Characteristics of ALD La2O3 capping layers using different lanthanum precursors in MOS devices with ALD HfO2, HfSiO, and HfSiOn gate dielectrics." Microelectric Engineering, 147 (2015) pp. 206-209.

Palvasaari, Jani, "Atomic Layer Deposition of Lanthanide Oxide Thin Films." Helsinki University of Technology, Inorganic Chemistry Publication Series, 2006, No. 6. p. 1-69.

Paivasaari J. "Atomic Layer Deposition of Lanthanide Oxide Thin Films" Helsinki University of Technology, Inorganic Chemistry Publication Series Espoo 2006 No. 6 (2006).

Krasnopolski, Michael, et al. "Homoleptic Gadolinium Amidinates as Precursors for MOCVD of Oriented Gadolinium Nitride (GdN) Thin Films". Inorganic Chemistry, p. 286-296; Dec. 11, 2012. (c)2012 American Chemical Society.

Paivasaari, Jani, et al. "Synthesis, Structure and Properties of Volatile Lanthanide Complexes Containing Amidinate Ligands; Application for Er2O3 Thin Film Growth by Atomic Layer Deposition". Journal of Materials Chemistry, p. 4224-4233, 2005, 15.

* cited by examiner

LOW HALIDE LANTHANUM PRECURSORS FOR VAPOR DEPOSITION

CROSS-REFERENCE TO RELATED APPLICATIONS

This application is a divisional of U.S. application Ser. No. 16/685,266, filed Nov. 15, 2019; which claims the benefit of priority to U.S. provisional application Ser. No. 62/772,450, filed Nov. 28, 2018. Both applications are incorporated herein by reference in their entirety.

BACKGROUND OF THE INVENTION

The invention relates generally to a composition comprising lanthanide such as lanthanum precursors containing 10.0 ppm or less and preferably <5.0 ppm of halide impurities such as fluorine, chlorine, bromine or iodine. The invention also relates to the method for deposition of lanthanum-containing films, such as lanthanum oxide, metal oxide doped with lanthanum oxide, lanthanum nitride and metal nitride doped with lanthanum nitride. Lanthanum-containing films are used in electronic industrial applications.

Thin films of rare earth oxides are of interest because of their potential use as dielectrics in microelectronics applications. In particular, lanthanum oxide ($La_2O_3$) is attractive for a number of reasons including its favorable conduction band offset at the $La_2O_3$/Si interface. This and other properties have led some to consider $La_2O_3$ or La-containing oxides for use as high-k materials in metal-oxide-semiconductor field effect transistors (MOSFETs) and capacitive devices. $La_2O_3$ has found use as a "capping layer" to adjust work functions in advanced MOSFETs.

Lanthanide complexes, such as lanthanum cyclopentadienyl and lanthanum amidinate complexes are widely used in electronic industry as precursors for chemical vapor deposition or atomic layer deposition of lanthanum-containing films. For various applications, semiconductor industry requires high purity precursors with trace metals and halide impurities well below single ppm's for metals and lower than 10.0 ppm for halides. This is because increasing the speed and complexity of semiconductor integrated circuits requires advanced processes that put extreme constraints on the level of contamination allowed on the surfaces of silicon wafers.

Metallic and halide contaminations on wafer surface are known to be a serious limiting factor to yield and reliability of CMOS based integrated circuits. Such contamination degrades the performance of the ultrathin SiO2 gate dielectrics that form the heart of the individual transistors. Halides impurities may migrate in the device and cause corrosion. The commonly reported mechanism for electrical field breakdown failure from iron contamination is the formation of iron precipitates at the Si—SiO2 interface, which frequently penetrate the silicon dioxide. Halide impurities present in lanthanum precursors may also cause corrosion of stainless steel containers used for delivery of lanthanum containing precursors to the deposition tool and transfer of iron and other stainless steel metal impurities to the lanthanum-containing film causing device failure.

Thus, precursors with low levels of halide contamination are highly desired. Purification methods to produce precursors with low halide contamination are also desired.

Commonly used precursors for deposition of lanthanum-containing films are lanthanum amidinates or $La(AMD)_3$, such as for example tris (N,N'-di-isopropylformamidinato) lanthanum (III) or $La(FAMD)_3$, lanthanum cyclopentadienyl complexes, such as for example tris(isopropylcyclopentadienyl) lanthanum (III) or La(iPrCp)3, and lanthanum diketonate complexes. Most common preparation of such lanthanum includes lanthanum halides as starting materials resulting in halide contamination.

Several methods were previously considered for purification of lanthanum compounds, for example crystallization and sublimation.

Hecker (U.S. Pat. No. 2,743,169 A) taught a sublimation method that can be used for metal chlorides separation and purification. Typically, sublimation is operated at reduced pressure, which can enhance the productivity and reduced operation temperature. The product is usually formed on a cold wall, and is harvested at the end of the purification process in an inert environment, as most metal halides are air and moisture sensitive.

For better solid product uniformity, fluidized bed is often used. Another advantage of using fluidized bed is to allow for automation of solid handling, which is difficult to implement with vacuum sublimation process. Schoener et al (U.S. Pat. No. 4,478,600) taught a method of using fluidization as part of aluminum chloride purification process yielding controlled product particle size. In the art, raw aluminum chloride was firstly generated through chlorination reaction at high temperature, in vapor phase, followed by a condensing stage to remove most solid impurities. The vapor is then supplied into a fluidization chamber to form product particles. Non-condensable contents, such as chlorine, carbon dioxide, and fluidizing gas are passed through a cooling fin for temperature control. Part of the gas is recycled by a pump, whereas the rest is vented through a scrubber. In this work, cold fluidization zone is provided for product condensation and particle formation.

Thus, the objective of this invention is to provide lanthanide cyclopentadienyl or lanthanide amidinate complex containing less than 10.0 ppm of chloride, bromide and fluoride, preferably less than 5.0 ppm halide, and more preferably less than 1.0 ppm halide.

Another objective of this invention is to provide lanthanide formamidinate or $La(FAMD)_3$ containing 50.0 ppm or less, 30.0 ppm or less, 20.0 ppm or less, 10.0 ppm or less, 5.0 ppm or less, or 2.0 ppm or less of all halide compounds combined.

Another objective of this invention is to provide a practical and scalable method for production of low halide lanthanide formamidinate.

BRIEF SUMMARY OF THE INVENTION

Accordingly, the present invention provides a low halide composition; a method and a system to purify a crude material comprising lanthanide amidinates, or more specifically lanthanum amidinate compounds to obtain the high purity composition comprising lanthanum amidinate compounds, and a delivery system to deliver the high purity composition comprising lanthanide amidinate compounds.

In one aspect, there is provided a lanthanide amidinate compound Ln(AMD)$_3$ having Formula I wherein $R^1$ is selected from the group consisting of hydrogen, and $C_1$ to $C_5$ linear or branched alkyl; $R^2$ and $R^2$ are independently selected from the group consisting $C_1$ to $C_5$ linear or branched alkyl; Ln is a lanthanide selected from the group consisting of La, Ce, Pr, Nd, Pm, Sm, Eu, Gd, Tb, Dy, Ho, Er, Tm, Yb, Lu;
the lanthanide amidinate compound comprises at least one halide impurity selected from the group consisting of chloride, bromide, fluoride, iodide and combinations thereof; wherein each of halide impurity ranges from 10.0 ppm or less, 5.0 ppm or less, 2.5 ppm or less, or 1.0 ppm or less; and all halide impurity combined ranges 50.0 ppm or less, 30.0 ppm or less, 20.0 ppm or less, 10.0 ppm or less, 5.0 ppm or less, or 2.0 ppm or less by weight.

The halide impurity comprises fluoride, chloride, iodide and/or bromide. The halide impurity forms volatile compounds that are deposited onto the film and have a negative effect on the dielectric constant.

In another aspect, there is provided practical and scalable method for production of high purity Lanthanide amidinate compounds; comprising
  a. providing the crude lanthanide amidinate material comprises lanthanide compound having Formula I wherein $R^1$ is selected from the group consisting of hydrogen, and $C_1$ to $C_5$ linear or branched alkyl; $R^2$ and $R^2$ each is independently selected from the group consisting of $C_1$ to $C_5$ linear or branched alkyl; and Ln is a lanthanide selected from the group consisting of La, Ce, Pr, Nd, Pm, Sm, Eu, Gd, Tb, Dy, Ho, Er, Tm, Yb, Lu; and
  the crude lanthanide amidinate material comprises at least one impurity selected from the group consisting of (i) halide impurities selected from the group consisting of LnCl$_x$(AMD)$_y$ (x+y=3), LnBr$_x$(AMD)$_y$ (x+y=3), LnF$_x$(AMD)$_y$ (x+y=3), LnI$_x$(AMD)$_y$ (x+y=3), wherein x or y is selected from 1 or 2, and combinations thereof; (ii) light impurity LnO(AMD)$_2$, and (iii) trace metals, and (iv) trace amounts of non-volatile impurities Ln$_2$O$_3$, Ln(OH)$_3$, or combinations;

b. providing zone 1 comprising at least one sublimer, zone 2 comprising at least one condenser; and zone 3 comprising at least one cooler; optionally a separation unit installed between zone 1 and zone 2 and selected from the group consisting of convoluted pathway, glass wool, filter, and combinations thereof; wherein zone 2 is in fluid communication with zone 1 and zone 3 is in fluid communication with zone 2;
  c. heating the crude lanthanum amidinate material contained in the at least one sublimer in zone 1 to get crude lanthanum amidinate material vapor separated from the halide impurities and the trace amounts of non-volatile impurities;
  d. passing the crude lanthanide amidinate material vapor from the zone 1 to the at least one condenser in zone 2 and condensing the crude lanthanide amidinate material vapor to form purified lanthanide amidinate material in the at least one condenser;
  e. passing the non-condensed light impurity LnO(AMD)$_2$ from the zone 2 into the at least one cooler in zone 3 to form solid light impurity;
  wherein the purified lanthanide amidinate material comprises each of halide impurity ranging from 10.0 ppm or less and all halide impurities combined ranging from 50.0 ppm or less.

In yet another aspect, there is provided a system for purifying a crude lanthanide amidinate material for vapor deposition comprising
  a) the crude lanthanide amidinate material comprises lanthanide amidinate compound having Formula I wherein $R^1$ is selected from the group consisting of hydrogen, and $C_1$ to $C_5$ linear or branched alkyl; $R^2$ and $R^2$ each is independently selected from the group consisting of $C_1$ to $C_5$ linear or branched alkyl; and Ln is a lanthanide selected from the group consisting of La, Ce, Pr, Nd, Pm, Sm, Eu, Gd, Tb, Dy, Ho, Er, Tm, Yb, Lu;
  b) zone 1 comprising at least one sublimer; wherein the crude lanthanide amidinate material is placed inside the at least one sublimer
  c) zone 2 comprising at least one condenser; wherein zone 2 is in fluid communication with zone 1; and
  d) zone 3 comprising at least one cooler; wherein zone 3 is in fluid communication with zone 2; and optionally
  e) a separation unit selected from the group consisting of convoluted pathway, glass wool, filter, and combinations thereof installed between zone 1 and zone 2;
  wherein
    the crude lanthanide amidinate material comprises 50 ppm or more at least one impurity selected from the group consisting of (i) halide impurities selected from the group consisting of LnCl$_x$(AMD)$_y$ (x+y=3), LnBr$_x$(AMD)$_y$ (x+y=3), LnF$_x$(AMD)$_y$ (x+y=3), LnI$_x$(AMD)$_y$ (x+y=3), wherein x or y is selected from 1 or 2, and combinations thereof; (ii) light impurities LnO(AMD)$_2$, (iii) trace metals, and (iv) trace amounts of non-volatile impurities Ln$_2$O$_3$, Ln(OH)$_3$, or combinations;

and purified lanthanide amidinate material is inside the at least one condenser in zone 2; and the purified lanthanide amidinate material comprises each of halide impurity ranging from 10.0 ppm or less and all halide impurities combined ranging from 50.0 ppm or less.

In yet another aspect, there is provided a delivery system or a vessel containing the purified lanthanide amidinate compound as disclosed above as a precursor.

DETAILED DESCRIPTION OF THE INVENTION

The method and the system described in present invention are generally to remove impurities from Lanthanide amidinate compounds through phase changing process.

The purified lanthanide amidinate compound Ln(AMD)$_3$ having Formula I wherein R$^1$ is selected from the group consisting of hydrogen, and C$_1$ to C$_5$ linear or branched alkyl; R$^2$ and R$^2$ are independently selected from the group consisting C$_1$ to C$_5$ linear or branched alkyl; Ln is a lanthanide selected from the group consisting of La, Ce, Pr, Nd, Pm, Sm, Eu, Gd, Tb, Dy, Ho, Er, Tm, Yb, Lu;

the lanthanide amidinate compound comprises at least one halide impurity selected from the group consisting of chloride, bromide, iodide, fluoride and combinations thereof; wherein each of halide impurity ranges from 10.0 ppm or less, 5.0 ppm or less, 2.5 ppm or less, or 1.0 ppm or less; and all halide impurity combined ranges 50.0 ppm or less, 30.0 ppm or less, 20.0 ppm or less, 10.0 ppm or less, 5.0 ppm or less, or 2.0 ppm or less by weight.

The raw or crude lanthanide such as lanthanum material mainly comprises up to 99.8 wt. % of primarily target lanthanide amidinate, and 1 ppm or more, 2 ppm or more, 5 ppm or more, 10 ppm or more, 50 ppm or more, impurities including but are not limited to (i) less volatile impurities such as LaCl$_x$(AMD)$_y$ (x+y=3), LaBr$_x$(AMD)$_y$ (x+y=3); LaI$_x$(AMD)$_y$ (x+y=3); LaF$_x$(AMD)$_y$ (x+y=3), wherein x and y is selected from 1 or 2; (ii) light impurities such as LaO(AMD)$_2$, (iii) trace metals, and (iv) trace amounts of non-volatile impurities e.g. La$_2$O$_3$, La(OH)$_3$, or combinations, In general, raw or crude material is heated to certain temperature, under which lanthanide compounds are vaporized into gaseous phase in a vaporization chamber. The lanthanide compound vapor is then condensed into collecting chambers, with one of the chamber being the main fraction collector where the pure lanthanide amidinate compounds is collected and harvested. Non-volatile impurities are left in the vaporization chamber as heel, whereas the low boiling point light impurities are collected into a chamber for light impurities collection.

One aspect of preparing pure lanthanide amidinate compounds is to remove less volatile lanthanide bromides, chlorides, iodides and fluorides from raw material. The final purified product contains 50.0 ppm or less, 30.0 ppm or less, 20.0 ppm or less, 10.0 ppm or less, 5.0 ppm or less, 2.0 ppm or less, or 1.00 ppm or less impurities.

According to the Thiele-McCabe method, separation of binary system at ppm level requires many theoretically plates, which is not available in vacuum sublimation or fluidized bed system.

Another aspect of preparing pure lanthanide amidinate compounds is to remove impurities with lower boiling point comparing to lanthanide formamidinate. These impurities can be separated through sublimation by utilizing different boiling points of product and impurities, through providing at least two temperature zones. Similarly, such separation can be achieved by utilizing different vapor pressures at a fixed temperature, and carrying low boiling impurities away with inert gas. By providing the suitable amount of inert gas, the Ln impurity can be kept in gaseous phase while most Ln(FAMD)$_3$ can be condensed, and, hence achieving separation.

Yet another aspect of this invention is to prevent product contamination with trace amounts of non-volatile impurities accumulated in sublimation heels. Filter media is used to filter vapor of amidinate compound from trace amounts of less volatile solid particulates which can be carried over into lanthanum from amidinate vapor by dusting or other mechanism. Other metal and halide impurities may also be carried over by the same mechanism.

In most embodiments, a purification system comprises of three series connected chambers: a sublimer where the raw material is vaporized, a condenser where the product is collected, and a cooler where the light impurity is collected.

Crude or raw lanthanide amidinate compound, which typically has 70-99.5 wt. % of lanthanide amidinate compound balanced with other impurities, is loaded in the sublimer, and heated to vaporize lanthanide amidinate compound. The vapor is passed through a heat traced connecting pipe into the condenser. lanthanide amidinate vapor is cooled down in condenser to form product. The light impurity, in vapor phase, is further passed through a heat traced connecting pipe to enter the cooler, and is cooled down and condensed in the cooler.

In certain embodiments, the vapor is forced to pass through chambers by applying vacuum. In certain embodiments, the vapor is forced to pass through chambers by inert gas flow. Yet in certain embodiments, both vacuum and inert gas flow can be applied simultaneously to force the vapor flow.

In certain embodiments, the product and light impurities are condensed by cold surfaces. In other embodiments, the product and light impurities are condensed by cold inert gas.

When condensed by cold inert gas, the condenser can be made into a fluidized bed so the product condensed in the gas stream can be nucleation seed and grow. By controlling the residence time in fluidized bed, uniformed product particle size and uniformed solid product purity can be achieved.

In all embodiment, a separation unit or particle trapper including but is not limited to convoluted pathway, glass wool, filter (such as a mediated filter), and combinations thereof; can be installed in the passage entering the condenser.

In certain embodiments, the chambers of the purification system are maintained at fixed temperature. In other embodiments, some chambers may vary temperature during purification process, to allow for better separation of light impurities.

Any of the above features can be combined with any of one or more other features. Other advantages, novel features, and uses of the present disclosure will become more apparent from the following detailed description of non-limiting embodiments when considered in conjunction with the accompanying drawings, which are schematic and which are not intended to be drawn to scale or to exact shape. In the figures, each identical, or substantially similar component that is illustrated in various figures is typically represented by a single numeral or notation. For purposes of clarity, not every component is labeled in every figure, nor is every component of each embodiment shown where illustration is not necessary to allow those of ordinary skill in the art to understand the invention.

Figure 1:
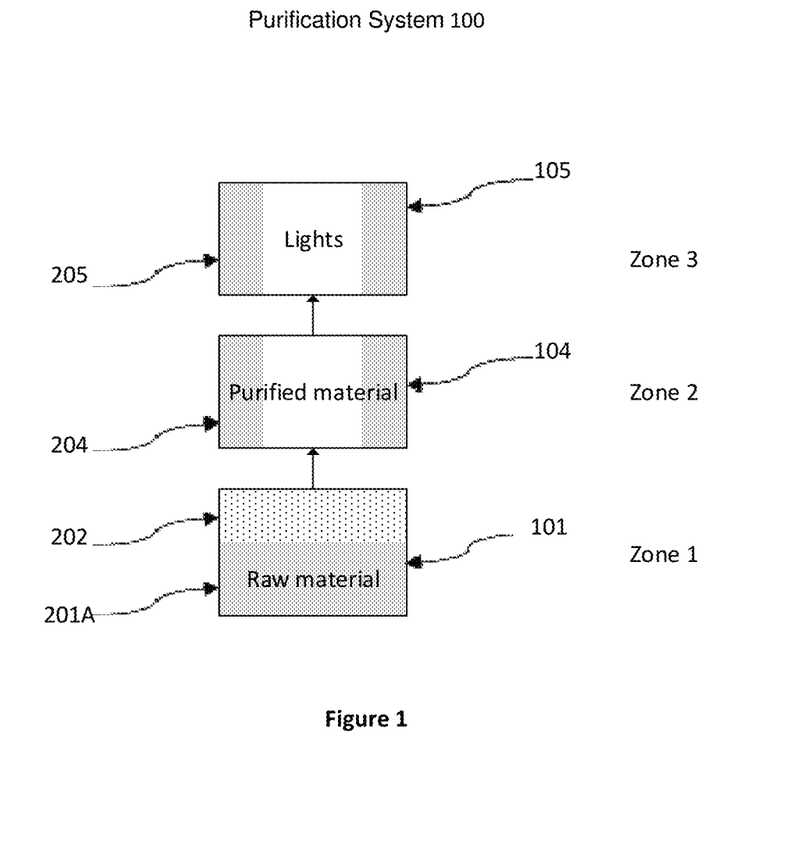
FIG. 1 is an exemplary purification system to remove halides.

An example of the present invention is shown in FIG. 1.

In some embodiments, the purification system 100 shown in FIG. 1 comprises at least one sublimer (101), at least one condenser (104), and at least one cooler (105).

The sublimer (101) is filled with raw amidinate compound material (201A). The sublimer is heated to a predetermined temperature, cause the raw material to vaporize and generate raw material vapor (202). The vapor is then enters the condenser (104) for product (204) collection. The none-condensed light impurity (205) is then passed into the cooler (105), and condensed there for forming solid light impurity (205).

Figure 2:
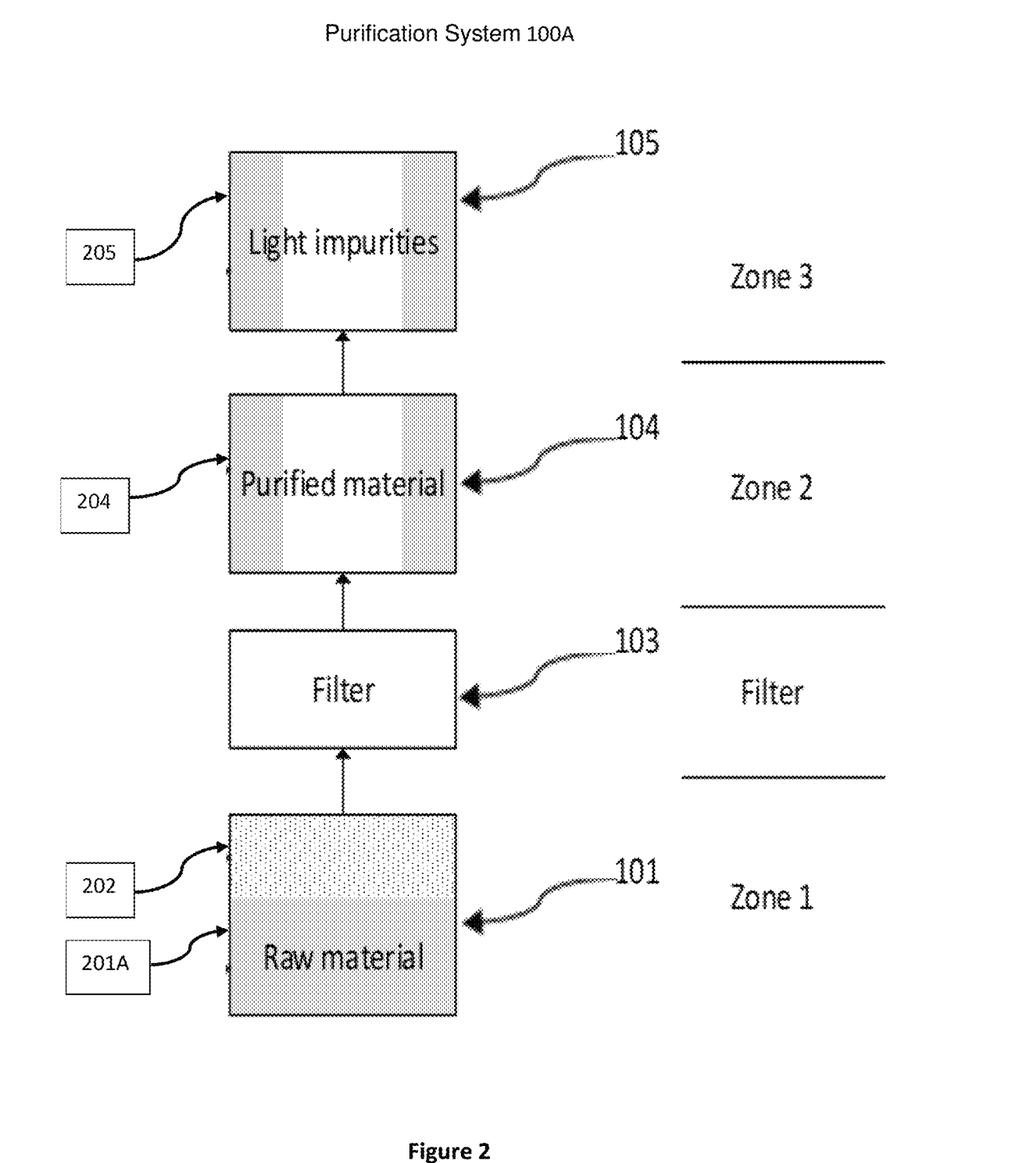
FIG. 2 is an exemplary purification system having a physical barrier (such as a filter) between raw material and purified material according to certain embodiments of the invention.

Another example of the present invention is shown in FIG. 2.

In some embodiments, the purification system 100A shown in FIG. 2 comprises at least one sublimer (101), at least one mediated filter (103), at least one condenser (104), and at least one cooler (105).

The sublimer (101) is filled with raw amidinate compound material (201A). The sublimer is heated to a predetermined temperature, cause the raw material to vaporize and generate raw material vapor (202). The vapor is then directed through a heat traced pipe (106), passed through a mediated filter (103) which serves as a physical barrier between raw material and purified material, and then enters the condenser (104) for product (204) collection. The none-condensed light impurity (205) is then passed into the cooler (105), and condensed there for forming solid light impurity (205).

In some embodiments, the purification system 100 or 100A is operated under vacuum. The system can be connected to a vacuum source for such purpose (not shown).

In other embodiments, the purification system 100 or 100A is operated using carrier gas, and is under slight positive pressure. This can be done by supplying an inert gas, such as N2, to the system (not shown).

Yet in other embodiments, the purification system 100 or 100A is operated under vacuum and using carrier gas, as vacuum and carrier gas can be supplied to the system at the same time.

In some embodiments, the product vapor supplied to the condenser is cooled by condenser surface. In other embodiments, the product vapor supplied to the condenser is cooled by a stream of cold inert gas (121) (not shown). Furthermore, the cold inert gas stream can be introduced through a distribution plate to form fluidized bed. Either way, the purified product (204) is collected in the condenser.

In some embodiments, the light impurity vapor (205) can pass the condenser by maintaining the condenser at high temperature at the beginning of the process, i.e., the same temperature as the sublimer. Once all the light impurities have been vaporized and passed through the condenser, the condenser temperature is reduced to cumulate product.

In other embodiments when cooling gas is used to condense the product, the condenser temperature can be maintained at a fix level under which the impurity vapor pressure is higher than the impurity concentration in the gaseous phase, and hence no impurity will condense in the condenser.

In some embodiments, the impurity vapor (205) supplied to the cooler is cooled by cooler surface. In other embodiments, the impurity vapor supplied to the cooler is cooled by a stream of cold inert gas (122) (not shown). Either way, the light impurity (205) is collected in the cooler.

In some embodiments, deep vacuum (<1 torr abs) is used for operation. The typical operation temperature for Zone 1 (see FIG. 1) is between 60° C. to 200° C., between 100° C. to 180° C., or between 120° C. to 160° C. The typical startup operation temperature for Zone 2 is between 80° C. to 200° C., between 100° C. to 180° C., or between 120° C. to 160° C., to remove the light impurities. After the light impurities are removed, the typical operation temperature for Zone 2 is between 20° C. to 100° C., 20° C. to 80° C., or between 20° C. to 60° C. The typical operation temperature for zone 3 is below 30° C. at any given time.

In some embodiments, fluidized bed is used in condenser for better solid product uniformity. One key element to achieve the above mentioned yield and economic aspect is to control the ratio of inlet fluidizing gas to the inlet amidinate compound vapor at the bottom of the condenser. It is important to keep the ratio low, so carryover or product by the gas is limited. Since this gas stream is also a cooling source for the inlet vapor, there is a lower limit for the ratio according to mass and heat balance. In general, the fluidizing gas will be heated majorly by the latent heat released from crystallization. Ideally, in the above mentioned temperature ranges, and ambient temperature $N_2$ gas is used.

Yet another key to achieve good crystal growth and high yield is to feed the condenser with high concentration of vapor. This can be achieved by providing high temperature to the sublimer, or limiting the carrying gas supplied to the sublimer. Combination of both options is preferred. In operation, it is preferable to keep the carrying gas to vapor boil up ratio to be <10:1, preferable <5:1, and more preferable <2:1, in molar unit. The sublimer should be heated to the upper limit mentioned above, depending on the operation pressure. That way, with high vapor concentration in the feed, less process residence time is achieved for the same amount of raw material, leading to less carryover of material as the total amount of gas passed through is reduced. In another embodiment lanthanide formamidinate is dissolved in inert solvent and the solution is eluted via adsorbent bed filled with inert adsorbent with high affinity for halide.

Solvent is removed from purified lanthanide formamidinate and lanthanide formamidinate is further purified by the methods described above.

In certain embodiments, delivery systems or vessels are provided for depositing lanthanide-containing film comprises lanthanide cyclopentadienyl or lanthanide amidinate complex containing <10.0 ppm, preferably <5.0 ppm and more preferably <2.5 ppm of Br; and <20.0 ppm, preferably <10.0 ppm of all halide impurity combined.

The vessel may be connected to deposition equipment known in the art by use of a valved closure and a sealable outlet connection.

Most preferably, the vessels may be constructed of high purity materials, including stainless steel, glass, fused quartz, polytetraflurorethylene, PFA®, FEP®, Tefzel® and the like. The vessels may be sealed with one or more valves. The headspace of the vessel is preferably filled with a suitable gas such as nitrogen, argon, helium or carbon monoxide.

EXAMPLES

Example 1

Vacuum Sublimation with Raw Lanthanum Formamidinate La(FAMD)$_3$ Having $R^1$ Hydrogen, $R^2=R^3$=Iso-Propyl Using Purification System 100

The purification system 100 shown in FIG. 1 was used.

600 gram of raw lanthanum formamidinate La(FAMD)$_3$ material was purchased from Strem Chemicals Inc., 7 Muliken Way, Newburyport, Mass. and placed into the sublimer 101. The halides and trace metals in the raw material were measured by Ion chromatography (IC) and were listed in Table I.

The system was evacuated to <0.5 torr abs pressure.

The sublimer was heated to 70° C. The condenser was heated to 70° C. for the first 5 hours. After 5 hours the sublime was heated to 160° C. and the condenser was run at room temperature (RT 20 to 25° C.) where the amidinate compound was condensed. The cooler was maintained at room temperature all the time

TABLE I

|  | Raw | Purified |
| --- | --- | --- |
| La(FAMD)$_3$ Assay | 99.7 wt. % | 99.9 wt. % |
| Chloride | 5.7 ppm | 1.8 ppm |
| Bromide | 583 ppm | 19.8 ppm |
| Li [No Gas] | 0.01 | 0.01 |
| Na [No Gas] | 0.05 | 0.04 |
| Mg [No Gas] | 0.01 | 0.01 |
| Al [No Gas] | 0.01 | 0.01 |
| K [H2] | 0.08 | 0.1 |
| Ca [H2] | 0.01 | 0.13 |
| Ti [No Gas] | 0.01 | 0.01 |
| Cr [H2] | 0.02 | 0.03 |
| Mn [No Gas] | 0.01 | 0.01 |
| Fe [H2] | 0.02 | 0.06 |
| Co [No Gas] | 0.01 | 0.01 |
| Ni [No Gas] | 0.01 | 0.01 |
| Cu [No Gas] | 0.01 | 0.02 |
| Zn [No Gas] | 0.01 | 0.07 |

The process was stopped after 24 hours.

197 gram of product was collected.

The halides and trace metals in the product were measured by Ion chromatography (IC), and listed in Table I.

The results indicated that sublimation reduced halide contents. However, chloride was around 1 ppm and bromide concentration was above 50 ppm.

The results also showed that the system was not efficient to reduce trace metals. Please notice the low level of the trace metals initially contained in the raw material.

Example 2

Vacuum Sublimation of Raw Lanthanum Formamidinate La(FAMD)$_3$ Having $R^1$=Hydrogen, $R^2=R^3$=Iso-Propyl Using Purification System 100A The purification system 100A shown in FIG. 2 was used. 193 grams of raw La(FAMD)3 material was purchased from Strem Chemicals Inc., 7 Muliken Way, Newburyport, Mass. and placed into sublimer. The halides and trace metals in the raw material were measured by Ion chromatography (IC) and were listed in Table 2.

TABLE II

|  | Raw | Product |
| --- | --- | --- |
| La(FAMD)$_3$ Assay | 99.72% | 99.8% |
| Chloride | 5.7 ppm | 0.9 ppm |
| Bromide | 563.8 ppm | 1.0 ppm |
| Li [No Gas] | 0.01 | 0.01 |
| Na [No Gas] | 2.19 | 0.04 |
| Mg [No Gas] | 0.05 | <0.03 |
| Al [No Gas] | 0.09 | 0.03 |
| K [H2] | 0.08 | 0.04 |
| Ca [H2] | 0.14 | <0.08 |
| Ti [No Gas] | <0.03 | <0.03 |
| Cr [H2] | 0.09 | 0.02 |
| Mn [No Gas] | 0.01 | 0.01 |
| Fe [H2] | 0.4 | 0.07 |
| Co [No Gas] | <0.02 | <0.02 |
| Ni [No Gas] | <0.03 | <0.03 |
| Cu [No Gas] | 0.05 | 0.02 |
| Zn [No Gas] | 0.06 | <0.05 |

A glass coarse fritted disc with porosity 40-60 micron was purchased from Chemglass Life Science LLC, 3800 N Mill Rd, Vineland, N.J. 08360 and used as the mediated filter 103.

The system was evacuated to <0.5 torr abs pressure.

The sublimer was heated to 140° C. The filter was heated to 200° C. The condenser was heated to 140° C. for the first 24 hours, and then reduced to room temperature where the amidinate compound was condensed. The cooler was maintained at room temperature all the time.

The process was stopped as the filter clogged the passage, usually after 48 hours.

40 grams of product was collected. The halides and trace metals in the product were measured by Ion chromatography (IC) in Table II.

The results indicated that chloride was effectively removed below 1 ppm by using system described in FIG. 2 and bromide was reduced to 1 ppm as well.

The results also showed that there was a consistency of the reduction of the trace metals, considering the low level of the trace metals initially contained in the raw material. The system used in this example was more effective to reduce the trace metals.

While the principles of the claimed invention have been described above in connection with preferred embodiments, it is to be clearly understood that this description is made only by way of example and not as a limitation of the scope of the claimed invention.

The invention claimed is:

1. A system for purifying a crude lanthanide amidinate material for vapor deposition comprising:
   a) the crude lanthanide amidinate material comprising a lanthanide amidinate compound Ln(AMD)$_3$ having Formula I wherein $R^1$ is selected from the group consisting of hydrogen, and $C_1$ to $C_5$ linear or branched alkyl; and $R^2$ and $R^3$ each is independently selected from the group consisting of $C_1$ to $C_5$ linear or branched alkyl; Ln is a lanthanide selected from the group consisting of La, Ce, Pr, Nd, Pm, Sm, Eu, Gd, Tb, Dy, Ho, Er, Tm, Yb, and Lu;
   b) zone 1 comprising at least one sublimer; wherein the crude lanthanide amidinate material is placed inside the at least one sublimer;
   c) zone 2 comprising at least one condenser; wherein the zone 2 is in fluid communication with the zone 1;
   d) zone 3 comprising at least one cooler; wherein the zone 3 is in fluid communication with the zone 2; and
   e) a separation unit selected from the group consisting of a convoluted pathway, glass wool, a filter, and combinations thereof; wherein the separation unit is installed between the zone 1 and the zone 2;
   wherein the crude lanthanide amidinate material comprises 50 ppm or more of at least one impurity selected from the group consisting of (i) halide impurities selected from the group consisting of LnCl$_x$(AMD)$_y$ (x+y=3), LnBr$_x$(AMD)$_y$ (x+y=3), LnI$_x$(AMD)$_y$ (x+y=3), and LnF$_x$(AMD)$_y$ (x+y=3), wherein x and y are selected from 1 or 2, and combinations thereof; (ii) light impurities LnO(AMD)$_2$, (iii) trace metals, and (iv) trace amounts of non-volatile impurities Ln$_2$O$_3$, Ln(OH)$_3$, or combinations thereof; and
   a purified lanthanide amidinate material is inside the at least one condenser in the zone 2; and the purified lanthanide amidinate material comprises 10.0 ppm or less of each individual halide impurity and 50.0 ppm or less of all halide impurities combined.

2. The system of claim 1, wherein the purified lanthanide amidinate material comprises 5.0 ppm or less of each individual halide impurity.

3. The system of claim 1, wherein the lanthanide amidinate compound Ln(AMD)$_3$ having Formula I, wherein R1 is hydrogen, and R2 and R3 are isopropyl, and is selected from the group consisting of La(FAMD)$_3$, Ce(FAMD)$_3$, Pr(FAMD)$_3$, Nd(FAMD)$_3$, Pm(FAMD)$_3$, Sm(FAMD)$_3$, Eu(FAMD)$_3$, Gd(FAMD)$_3$, Tb(FAMD)$_3$, Dy(FAMD)$_3$, Ho(FAMD)$_3$, Er(FAMD)$_3$, Tm(FAMD)$_3$, Yb(FAMD)$_3$, and Lu(FAMD)$_3$.

4. The system of claim 1, wherein the lanthanide is lanthanum and $R^1$ is hydrogen.

5. The system of claim 1, wherein the purified lanthanide amidinate material comprises 2.0 ppm or less of each individual halide impurity.

6. The system of claim 1, wherein the purified lanthanide amidinate material comprises 1.0 ppm or less of each individual halide impurity.

7. A method for purifying a crude lanthanide amidinate material for vapor deposition comprising:
   a) providing the crude lanthanide amidinate material comprising a lanthanide compound Ln(AMD)$_3$ having Formula I wherein $R^1$ is selected from the group consisting of hydrogen, and $C_1$ to $C_5$ linear or branched alkyl; and $R^2$ and $R^3$ each is independently selected from the group consisting of $C_1$ to $C_5$ linear or branched alkyl; Ln is a lanthanide selected from the group consisting of La, Ce, Pr, Nd, Pm, Sm, Eu, Gd, Tb, Dy, Ho, Er, Tm, Yb, and Lu; and
   further comprising at least one impurity selected from the group consisting of (i) halide impurities selected from the group consisting of LnCl$_x$(AMD)$_y$ (x+y=3), LnBr$_x$(AMD)$_y$ (x+y=3), LnI$_x$(AMD)$_y$ (x+y=3), and LnF$_x$(AMD)$_y$ (x+y=3), wherein x and y are selected from 1 or 2, and combinations thereof; (ii) light impurity LnO(AMD)$_2$, and (iii) trace amounts of non-volatile impurities Ln$_2$O$_3$, Ln(OH)$_3$, or combinations thereof;
   b) providing zone 1 comprising at least one sublimer, zone 2 comprising at least one condenser; and zone 3 condenser, zone 3 comprising at least one cooler, and a separation unit installed between the zone 1 and the zone 2, wherein the separation unit is selected from the group consisting of a convoluted pathway, glass wool, a filter, and combinations thereof; wherein the zone 2 is in fluid communication with the zone 1 via the separation unit, and wherein the zone 3 is in fluid communication with the zone 2;
   c) feeding the crude lanthanide amidinate material of step a) into the at least one sublimer of zone 1 of step b) and heating the crude lanthanide amidinate material contained in the at least one sublimer in the zone 1 to generate a crude lanthanide amidinate material vapor;
   d) passing the crude lanthanide amidinate material vapor from the zone 1 to the at least one condenser in the zone 2 through the separation unit and condensing a portion of the crude lanthanide amidinate material vapor in the at least one condenser to form a purified lanthanide amidinate material;
   wherein the purified lanthanide amidinate material formed in the at least one condenser comprises 10.0 ppm or less of each individual halide impurity and 50.0 ppm or less of all halide impurities combined.

8. The method of claim 7, wherein the temperature of zone 1 ranges between 60° C. and 200° C., the temperature of zone 2 ranges between 80° C. and 200° C., and the temperature of zone 3 is 30° C. or less.

9. The method of claim 7, wherein the lanthanide amidinate compound $Ln(AMD)_3$ having Formula I, wherein R1 is hydrogen, and R2 and R3 are isopropyl, and is selected from the group consisting of $La(FAMD)_3$, $Ce(FAMD)_3$, $Pr(FAMD)_3$, $Nd(FAMD)_3$, $Pm(FAMD)_3$, $Sm(FAMD)_3$, $Eu(FAMD)_3$, $Gd(FAMD)_3$, $Tb(FAMD)_3$, $Dy(FAMD)_3$, $Ho(FAMD)_3$, $Er(FAMD)_3$, $Tm(FAMD)_3$, $Yb(FAMD)_3$, and $Lu(FAMD)_3$.

10. The method of claim 7, wherein the lanthanide is lanthanum and $R^1$ is hydrogen.

11. The method of claim 7, wherein the purified lanthanide amidinate material comprises 5.0 ppm or less of each individual halide impurity.

12. The method of claim 7, wherein the purified lanthanide amidinate material comprises 2.0 ppm or less of each individual halide impurity.

13. The method of claim 7, wherein the purified lanthanide amidinate material comprises 1.0 ppm or less of each individual halide impurity.

* * * * *